United States Patent [19]

Toker et al.

[11] Patent Number: 5,142,557

[45] Date of Patent: Aug. 25, 1992

[54] CCD AND PHOSPHOR SCREEN DIGITAL RADIOLOGY APPARATUS AND METHOD FOR HIGH RESOLUTION MAMMOGRAPHY

[75] Inventors: Emre Toker; Tim B. Hunter; Hans Roehrig, all of Tucson, Ariz.

[73] Assignee: Photometrics Ltd., Tucson, Ariz.

[21] Appl. No.: 633,212

[22] Filed: Dec. 21, 1990

[51] Int. Cl.$^5$ .............................................. A61B 6/04
[52] U.S. Cl. ..................................... 378/37; 378/62; 378/64; 378/98; 378/145; 378/901; 358/111
[58] Field of Search .................... 378/62, 98, 4, 99.37, 378/64, 65, 145, 146, 901; 358/111; 250/370.08, 370.09, 363.04, 363

[56] References Cited

U.S. PATENT DOCUMENTS

| | | | |
|---|---|---|---|
| 3,824,399 | 7/1974 | Bjork et al. | 250/336 |
| 4,015,126 | 3/1977 | Herrington | 250/320 |
| 4,284,889 | 8/1981 | Kato et al. | 250/355 |
| 4,346,406 | 8/1982 | Kato et al. | 358/110 |
| 4,349,739 | 9/1982 | Annis | 378/99 |
| 4,562,464 | 12/1985 | Kurihara | 378/99 |
| 4,580,054 | 4/1986 | Shimoni | 250/363.04 |
| 4,590,518 | 5/1986 | Fenster et al. | 378/99 |
| 4,602,156 | 7/1986 | Asai et al. | 250/327.2 |
| 4,721,856 | 1/1988 | Saotome et al. | 250/327.2 |
| 4,730,350 | 3/1988 | Albert | 378/99 |
| 4,737,641 | 4/1988 | Lange et al. | 250/327.2 |
| 4,814,616 | 3/1989 | Saotome | 250/327.2 |
| 4,814,617 | 3/1989 | Goto | 250/327.2 |
| 4,818,877 | 4/1989 | Ayrai et al. | 250/484.1 |
| 4,821,727 | 4/1989 | Levene et al. | 128/653 |
| 4,827,129 | 5/1989 | Tressl et al. | 250/327.2 |
| 4,852,137 | 7/1989 | Mackay | 378/62 |
| 4,943,987 | 7/1990 | Asahina et al. | 378/62 |
| 4,946,238 | 8/1990 | Sashin et al. | 378/99 |
| 5,003,571 | 3/1991 | Kido et al. | 378/37 |

Primary Examiner—Janice A. Howell
Assistant Examiner—Kim-Kwok Chu
Attorney, Agent, or Firm—Herbert M. Shapiro

[57] ABSTRACT

A system for locating a region of varying density in biological tissue such as a breast includes a controlled x-ray source for directing x-rays through the breast, a phosphor screen positioned to receive x-rays exiting from the tissue and producing light in response thereto, a cooled, slow scan CCD camera, a variable magnification optical system positioned to receive light emitted by the phosphor screen and directing it to the cooled, slow scan CCD camera, a high resolution monitor, and a control system receiving signals from the cooled, slow scan CCD camera and digitizing the signals to produce digital data representative of the densities of various locations of the tissue. The control system includes a processor operated to determine a signal-to-noise ratio of light received by the cooled, slow scan CCD camera from the variable magnification optical system and to control the intensity of x-rays in response to the signal-to-noise ratio to determine locations of the object at which the corresponding densities exceed a certain level. The addresses of such locations are stored. The variable magnification optical system is controlled to focus and enlarge "digitally marked" locations of the object so images thereof substantially fill a screen of the monitor. In one described embodiment, the system is used in conjunction with a radiopaque needle localization process to rapidly and precisely identify locations of high density breast tissue which are likely tumor and/or microcalcification sites.

3 Claims, 6 Drawing Sheets

CCD AND PHOSPHOR SCREEN DIGITAL RADIOLOGY APPARATUS AND METHOD FOR HIGH RESOLUTION MAMMOGRAPHY

BACKGROUND OF THE INVENTION

The invention relates to apparatus and methods for improving the speed and accuracy of biological x-ray radiology such as those used in mammography, lithotripsy, and bone imaging, and to apparatus and techniques for reducing the required x-ray dosage, improving contrast resolution, improving the speed of the process, and improving the speed and convenience of radiopaque needle localization and fine needle aspiration biopsy techniques.

Figure 1:
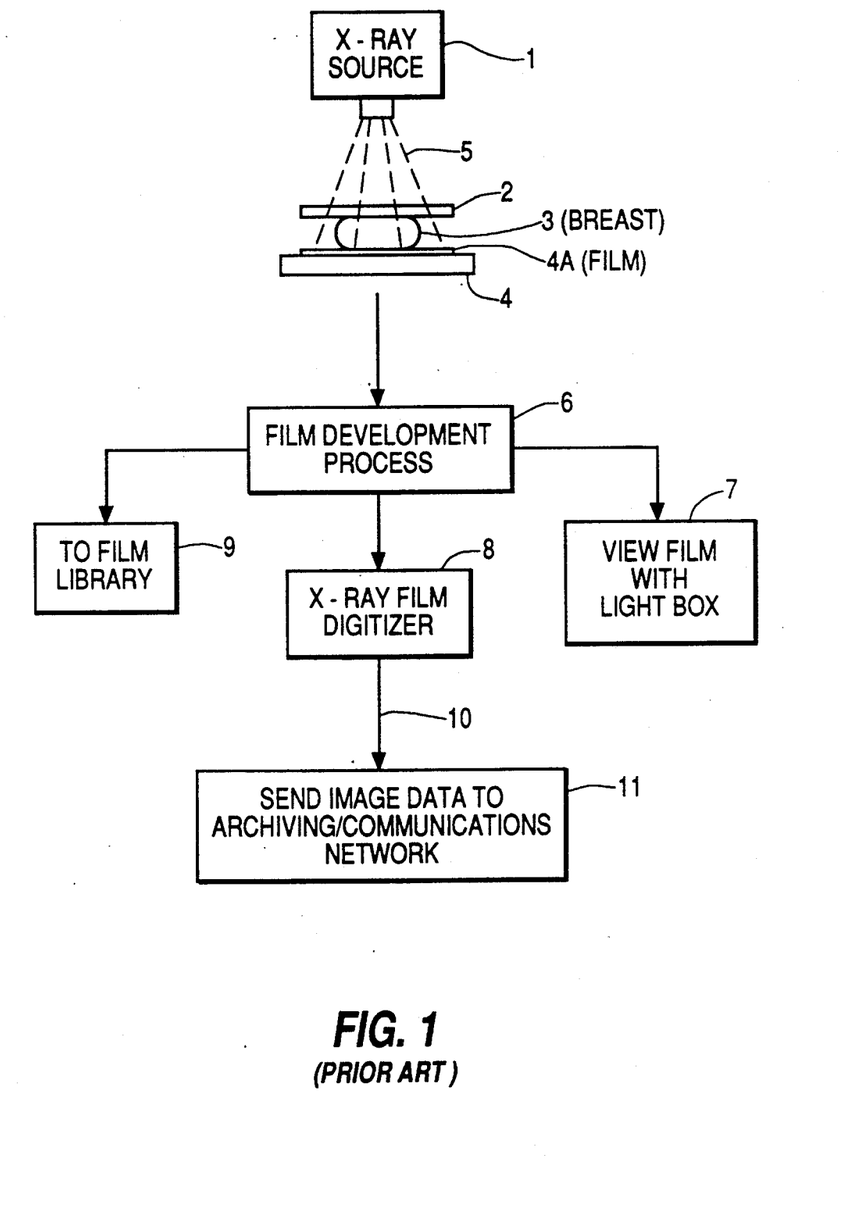
FIG. 1 is a block diagram of a conventional screen/film x-ray mammography system using radiographic film to record x-ray patterns.

In conventional mammography, a woman sits in front of a mammography screen and places her breast, designated by numeral 3 in FIG. 1, on a support 4 having thereon or therein a screen/film detector 4A that is sensitive to x-rays. A breast compressor plate 2 that is transparent to x-rays presses against the top of breast 3 to flatten it and prevent any movement of it during the mammography process. An x-ray source 1 is turned on to produce x-rays 5. The density of a tumor or microcalcification in the breast is different than that of healthy breast tissue, and may appear as a lighter or darker area on radiographic film 4A. Density variations which may be indicative of lesions appear as variations in darkness of an image on radiographic film 4A.

After the exposure of film 4A to the x-rays exiting from breast 3, film 4A is developed using conventional processes, as indicated in block 6 of FIG. 1. This process typically requires 1½ to 5 minutes. The film negative obtained from the development process can be used in various ways. The most common way of using the film negative is to simply place it on a light box. The physician then can inspect it and hopefully visually recognize any image density variations that suggest the presence of a tumor or group of microcalcifications. Sometimes a digitizing machine is utilized to scan and completely digitize the image appearing on the film negative and store the digitized image data in a computer. The digitized image usually is used for archival purposes and research purposes. (At the present state of the art, the best image contrast resolution presently available is 8 to 10 bits per pixel.) The computer then can perform various known image processing operations on the data in order to identify various features of the image. Arrow 10 in FIG. 1 designates storage of digitized data, and block 11 represents processing of the image data. The developed film negative typically is stored in a library archive after light box viewing or digitization, as indicated in block 9 of FIG. 1.

There are a number of problems common to the above-described conventional mammography techniques and other biological radiology processes. One problem is that film development processing is much slower than is desirable. Another problem with conventional mammography, lithotripsy, and bone imaging is that x-ray dosages are higher than desirable. The human body should be exposed to as few x-rays as is consistent with the effectiveness of the particular diagnostic x-ray system. Unfortunately, it sometimes is not known until after the step indicated in block 7 and/or 11 of FIG. 1 whether the film is underexposed or overexposed and whether more x-rays of the woman's breast consequently are needed to accurately analyze any possible tumors or microcalcifications. Furthermore, the 8-to-10 bit intensity resolution per pixel contrast which is presently achievable is not as high as desirable.

Another conventional mammography technique utilizes the apparatus and method described above further augmented by a radiopaque needle localization technique. A metal needle is inserted into a particular location of the woman's breast as she stands in front of the mammography screen. The needle is moved to various locations of the woman's breast on a trial-and-error basis to "close in" on the abnormal density locations indicated by the developed films. X-rays are taken and developed for each insertion, until the tip of the needle is located precisely at the site of a possible tumor or group of microcalcifications which have been visually located in accordance with the procedure of block 7 in FIG. 1. Some prior techniques feed the x-ray films to a film digitizer. A computer reads the resulting digitized intensity values and computes how deep the needle tip should be. In a procedure called stereotactic biopsy, two exposures are taken using the same film. The x-ray source is tilted 45 degrees in opposite directions for the two exposures. A computer or an operator measures the displacement of a lesion on the film between the two exposures and from that information computes the depth of the lesion within the breast.

The procedure of obtaining a useable image and moving the needle on a trial-and-error basis to locate it precisely at the site of a likely tumor is time-consuming and very uncomfortable to the woman, who must remain sitting at the mammography screen, without moving, until the needle is properly located. After the needle has been properly located, the patient then may go to surgery for a biopsy, wherein the surgeon follows an incision along a needle to the tip of the needle and removes tissue located thereat for analysis. Alternately, a radiopaque needle biopsy aspiration technique can be performed while the breast remains compressed by plate 2.

It is known in lithotripsy, in which a kidney stone or gallstone is located by ultrasound imaging techniques and high intensity sonic energy is then focused on the kidney stone to shatter it, that it would be desirable to obtain faster determination of the location of the kidney stone or gallstone because the patient is maintained under anesthesia during the procedure. Increase of risk to the patient could be reduced substantially by reducing the time under anesthesia. Similarly, known radiological bone imaging techniques utilize x-rays and CCD (charge-coupled device) cameras, but the amount of time required to obtain images and is greater than desirable, and the amount of x-ray dosage required is greater than desirable.

CCD's have been used in radiological imaging, and are known to have inherent resolution capable of matching or exceeding the resolution of developed x-ray film. See "HIGH RESOLUTION DIGITAL RADIOGRAPHY UTILIZING CCD PLANAR ARRAY", by Shaber, Lockard, and Boone, presented in December 1989, and published in SPIE, Volume 914, Medical Imaging II, page 262-269. (The present assignee provided the cooled, slow scan CCD camera and a three stage Peltier thermoelectric cooler for the CCD planar array utilized in the camera for the reported experiments. However, the apparatus and technique described fails to enable a user to reduce the x-ray dosage to the minimum levels needed to obtain the high level of spatial resolution reported and to overcome some of the disadvantages of prior radiopaque needle localization techniques.

There is a need for a technique to rapidly obtain results of x-ray mammography, lithotripsy, and bone imaging with spatial resolution and contrast resolution equal to or better than those achievable by conventional x-ray film negatives, while avoiding the time-consuming techniques and patient discomfort of prior mammography techniques and prior needle localization techniques, lithotripsy techniques, bone imaging techniques, and radiation therapy techniques.

Cooled, slow scan, low noise CCD cameras have been used in astronomy, and also have been used in various industrial radiography applications, but with much higher dosages of x-rays than is permissible in mammography and other medical applications. As used herein, the term "cooled, slow scan" refers to CCD arrays in which the CCD array is cooled, for example, by means of thermoelectric devices, to temperatures at which thermal noise is reduced to levels at which diagnostic quality radiological images can be produced. Cooled, slow scan CCD cameras presently marketed by the assignee have CCD array operating temperatures of about −20 degrees Centigrade or lower. The "slow scan" terminology refers to scanning rates that are substantially less than conventional video scan rates of 30 frames per second. The "slow scan" terminology also refers to devices in which double correlated sampling and dual slope integration techniques are electronically accomplished to minimize electronic noise. This produces improved contrast resolution and increased signal-to-noise ratios. However, it is quite problematical to determine whether such cooled, slow scan CCD cameras and techniques are practical in particular medical radiology applications such as in mammography, because medical radiology applications require minimum possible x-ray dosages, very high contrast resolution and spatial resolution. In some cases, short times for image generation are desirable, especially for needle localization techniques. Some radiological applications, for example, coronary angiography, require fast frame rates, e.g. 30 frames per second. This is inconsistent with the high signal-to-noise ratios needed to achieve the high resolutions, because fast cooled, slow scan CCD camera scanning rates needed for fast image generation result in low signal-to-noise ratios.

SUMMARY OF THE INVENTION

It is an object of the invention to reduce the x-ray dosage required in biological x-ray radiology while achieving acceptable contrast resolution and spatial resolution.

It is another object of the invention to achieve higher contrast resolution than is presently achievable for known x-ray mammography, lithotripsy, or bone imaging film techniques and known stimulated phosphor screen/cooled, slow scan CCD camera techniques.

It is another object of the invention to achieve more accurate results in less time and with less inconvenience and discomfort to the patient than is achievable, for example, in conventional x-ray mammography, especially when known radiopaque needle localization and/or known fine needle biopsy aspiration techniques are used.

It is another object of the invention to decrease the delay in obtaining useable "film-quality" images in biological x-ray radiology procedures.

Briefly described, and in accordance with one embodiment thereof, the invention provides a system for locating a region of varying density in biological tissue, such as a breast, including a controlled x-ray source for directing x-rays through the tissue, a phosphor screen positioned to receive x-rays exiting from the tissue and producing light in response to the exiting x-rays, a cooled, slow scan CCD camera, a variable magnification optical system or a fiber optic reducer positioned to receive light emitted by the phosphor screen and directing it to the cooled, slow scan CCD camera, a high resolution monitor, and a control system receiving signals from the cooled, slow scan CCD camera and digitizing the signals to produce digital data representative of the densities of various locations of the breast. The x-ray dosage is reduced by repetitively reading a serial register in the cooled, slow scan CCD camera during x-ray exposure and by determining in response to the contents of the serial register when sufficient x-ray dosage has passed through the tissue to produce an acceptable x-ray image and then immediately terminating the x-ray dosage by shutting off the x-ray source. The CCD array then is read out and the image is presented to a radiologist. The control system in another embodiment in which the variable magnification optical system is used, includes a processor operated to determine a signal-to-noise ratio of light received by the cooled, slow scan CCD camera from the variable magnification optical system, to control the dosage of x-rays produced by the x-ray source in response to the signal-to-noise ratios to determine locations of the object at which the corresponding densities deviate by a prescribed amount. Such locations then are digitally marked by storing addresses of such locations. The variable magnification optical system then is operated to focus and enlarge selected digitally marked locations of the object so images thereof substantially fill a screen of the monitor. In one described embodiment of the invention, either of the above systems is used in conjunction with a radiopaque needle localization process to rapidly and precisely identify locations of high density breast tissue which are likely tumor and/or microcalcification sites, with minimum discomfort and inconvenience to the patient. The x-ray dosage is reduced to the point that only the radiopaque needle distinctly appears in the image during the needle location procedures, thereby greatly reducing x-ray exposure of the patient.

DETAILED DESCRIPTION OF THE PRESENTLY PREFERRED EMBODIMENTS

Figure 2:
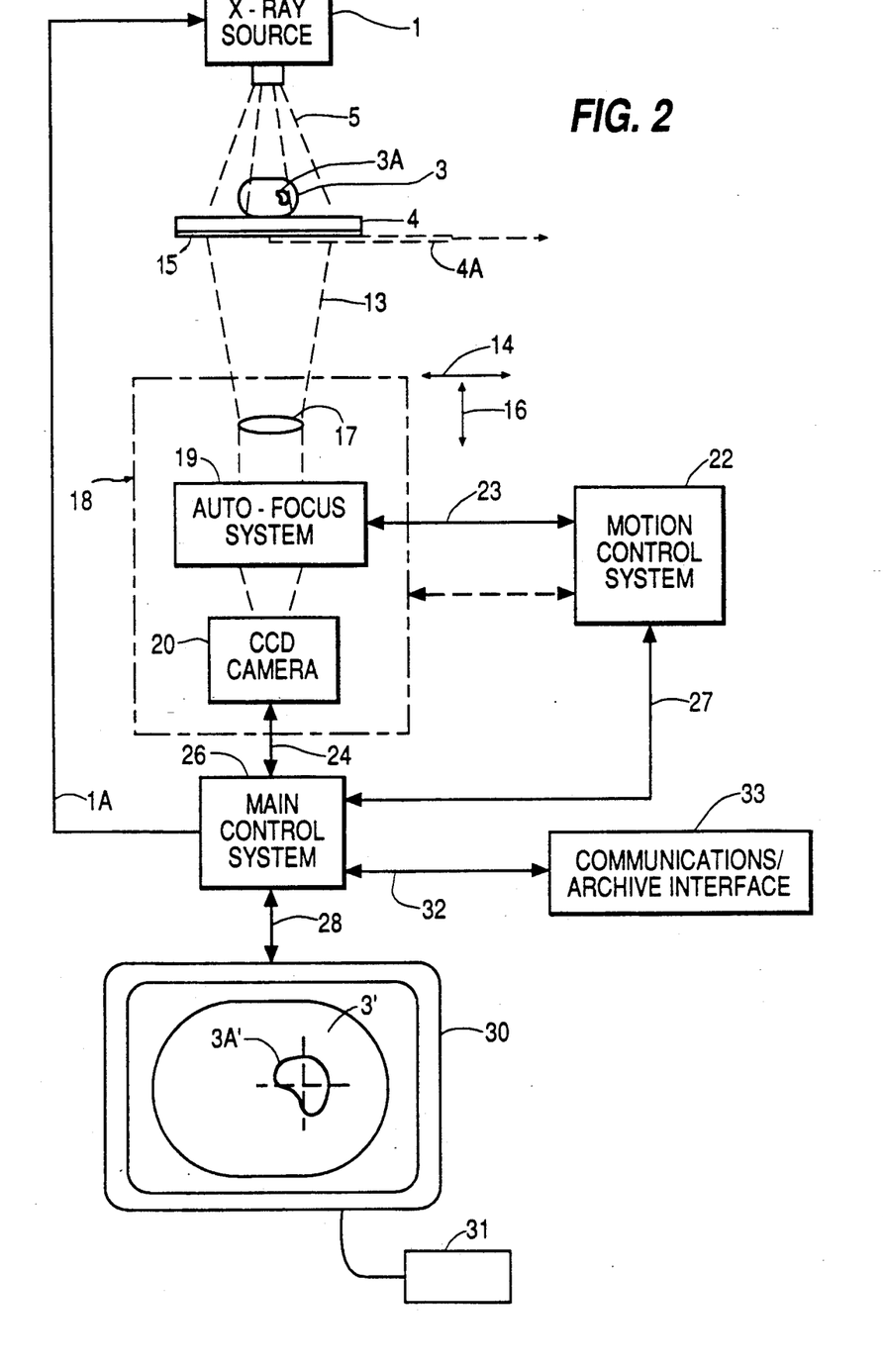
FIG. 2 is a diagram illustrating the CCD and phosphor screen digital radiology apparatus of the present invention to achieve rapid, high resolution mammography with low x-ray doses.

FIG. 2 illustrates a high resolution x-ray system 50 that includes the x-ray source 1 and a plate 2 compressing breast 3 to prevent any movement thereof. A region 3A of high density breast tissue is shown. (Note, that object 3 can be tissue other than a breast, in which case plate 2 may not be needed.) As in the conventional mammography x-ray apparatus of FIG. 1, breast 3 is securely compressed between support 4 and plate 2. A phosphor screen 15 is positioned in or on support 4 and receives the x-rays 5 that have passed through and have been partially absorbed by breast 3 in accordance with density of tissue therein. A suitable phosphor screen is Model Min-R manufactured by Kodak, with an emission wavelength of 550 nanometers.

The x-ray photons 5 emitted from the x-ray source 1 pass through breast 3 and impinge on phosphor screen 15. Phosphor screen 15 absorbs a certain percentage of the x-ray photons. Each x-ray photon generates a somewhat variable number of light photons 13 determined by the absorption efficiency and the emission efficiency of the phosphor screen. In response to the energy of the x-rays, phosphor screen 15 emits light, the downward portion 13 of it being captured by lens 17. The brightness of the light emitted from a particular point of phosphor screen 15 is proportional to the intensity of the x-rays exiting from a corresponding point of breast 3. (Optionally, the light 13 can be intercepted by radiographic film 4, which can be developed and used for visual inspection by a physician.)

It should be noted that presently available two-dimensional CCD arrays are much smaller in size than the physical size of a horizontal cross-section through a woman's breast. It therefore may be desirable to have an automatic demagnification-and-focusing system 19 to demagnify and accordingly refocus the image produced by phosphor screen 15 in response to x-rays 5 to the size of the lens of cooled, slow scan CCD camera 20.

A suitable optical interface 18 is provided between the phosphorous screen 15 and cooled, slow scan CCD camera 20 to demagnify the image emitted by the phosphor screen into the aperture of cooled, slow scan CCD camera 20. Optical interface 18 includes lens 17, which is a 50 millimeter coupling lens that may have an f number of 0.7. Optical interface 18 also includes an automatic focusing system 19, subsequently described. Coupling lens 17 collects as many light photons as possible from phosphor screen 15 and demagnifies the image onto the lens of cooled, slow scan CCD camera 20. Cooled, slow scan CCD camera 20 can be a high sensitivity, slow scan, cooled CCD camera, such as a Model CH250 marketed by the assignee, which is positioned to receive the demagnified, focused image from optical interface 18.

Figure 3:
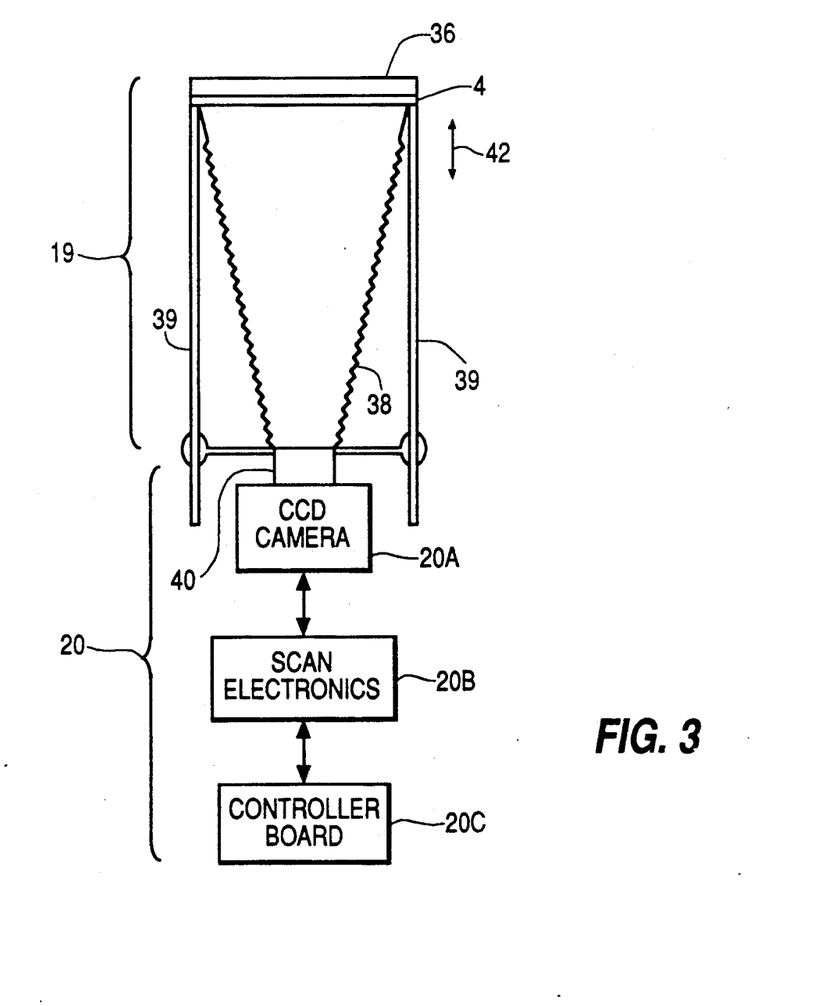
FIG. 3 is a diagram including an automatic demagnification and refocusing system, cooled, slow scan CCD camera, and camera scan electronics included in the system of FIG. 2.

FIG. 3 shows part of optical interference 18 of FIG. 2 in more detail A light-tight flexible bellows 38 in FIG. 3 prevents outside light from entering lens 40 and passing into cooled, slow scan CCD camera 20A.

Automatic focusing system 19 is controlled by signals 23 (FIG. 2) from a motion control system 22, which in turn is controlled by signals 27 from a main control system 26. Main control system 26 includes a MACINTOSH computer available from Apple Computer Company and NUBUS camera controller software commercially available from the present assignee. Main control system 26 digitizes the information received from cooled, slow scan CCD camera 20, so that quantified information about the intensity of light incident on each pixel is received. Main control system 26 communicates via signals IA with x-ray source 1 and motion control system 22 to instruct camera 20A to zoom to a particular distance as indicated by arrows 42 in FIG. 3 so that the object of interest will cover the entire screen of monitor 30 and obtain a high resolution image. Main control system 26 also supplies control signals IA to the x-ray source 1 to allow automatic corresponding reduction of the x-ray dosage to the lowest level commensurate with the signal-to-noise ratio or the image resolution needed for the present phase of operation of system 50.

Motion control system 22 is capable of varying the distance of cooled, slow scan CCD camera 20 from the carbon fiber window 36 shown in FIG. 3, which has a maximum field of view of 16 centimeters by 16 centimeters. Motion control system 22 can vary the distance between the camera head and carbon fiber window from 48 centimeters to 66 centimeters, producing variable demagnification. Optical interface 40 can be achieved by the use of a f0.7, 50 millimeter Nikkor lens system and appropriate lens extenders. Blocks 20B and 20C in FIG. 3 designate Model CE200 scan electronics available from the present assignee and capable of scanning at 500 kilopixels per second, and a NUBUS controller card also available from the present assignee, respectively.

Cooled, slow scan CCD camera 20 sends CCD signals 24 (FIG. 2) in a standard format to control system 26. In response to CCD signals 24, main control system 26 produces digital signals representing the light image produced by phosphor screen 15 and representing the image of breast 3 and transmits them to an archiving and communication system 33 for storage. Signals 28 from main control system 26 are standard video signals that are sent to a conventional high resolution monitor 30, which displays an image 3' of breast 3, with a darker image 3A' of the high density tissue 3A. A radiologist manipulates a conventional mouse 31 to move a cursor on monitor 30, and produces signals 28 that inform main control system 26 of the location of the high density tissue 3A, thereby "digitally marking" that location.

Figure 2A:
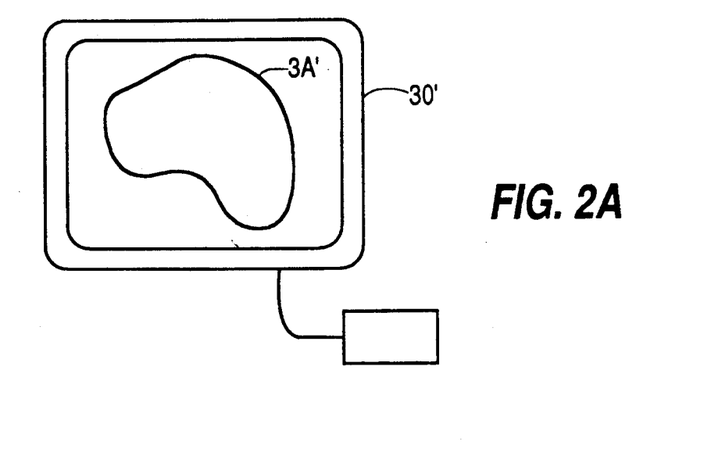
FIG. 2A is a diagram showing an optically zoomed high resolution image on the monitor shown in FIG. 2.

A control signal (not shown) initiated by the radiologist allows amplification of image 3' with very high resolution by causing automation focusing system 19 to focus on the digitally marked portion of breast 3, producing the amplified high resolution image 3A' as shown in FIG. 2A. To achieve digital marking, the image data is acquired and stored in the following format: each pixel of the CCD detector is identified by its X and Y coordinates, followed by the corresponding intensity level at that pixel. The X and Y coordinates are calibrated to identify locations on the phosphor screen. When the radiologist moves the cursor to identify a particular area within the image displayed on monitor 30, the coordinates of the corresponding area of breast 3 defined by the radiologist are stored in a computer. Then motion control system 22 is activated, and cooled, slow scan CCD camera 20 is electronically positioned and focused by means of automatic focusing system 19 to limit the field of view to the digitally marked region of interest.

Cooled, slow scan CCD camera 20 has associated with it conventional camera electronics that need not be described in detail, except to note that the electrical signals produced in response to light that is emitted by phosphorous screen 15, demagnified by automatic focusing system 19 into the lens of cooled, slow scan CCD camera 20, and impinging upon individual CCD cells thereof are converted to suitable digital data having a resolution of 12 or more digital bits per pixel. As previously indicated, this high sensitivity equals or exceeds the sensitivity of presently available radiographic film. In cooled, slow scan CCD camera 20, the CCD detector is cooled and operated at a temperature of about 0 to −50 degrees Centigrade, which limits thermal noise. Cooled, slow scan CCD camera 20 employs "slow-scan" electronics (i.e., substantially slower scan rate than standard video scan rates) that limit electrical noise. High signal-to-noise ratio thereby is achieved, resulting in high contrast resolution which is desirable for mammography and other biological radiology imaging applications.

In accordance with the above-described embodiment of the present invention, an initial digital image is obtained for the entire breast 3, by operating x-ray source 1 in response to main control system 26 to produce a sufficiently high x-ray dose to obtain an initial diagnostic quality image of the entire breast. That image is processed and stored in a computer memory in main control system 26. The stored image is immediately evaluated by a radiologist. The possible locations of tumors or microcalcification are "digitally marked" in the computer memory so that they can be instantly relocated.

Then, the x-ray dosage is reduced considerably in accordance with the technique subsequently described with reference to FIG. 4. In the embodiment of FIG. 2, the automatic focusing system then collimates the reduced x-ray dose on a much smaller region of breast 3 which corresponds to one of the digitally marked locations. This procedure is repeated for all of the other digitally marked high density locations of the breast, and results in a much lower overall x-ray dosage to the patient because high doses are applied only to the high density tissue regions of the breast, which high density tissue regions constitute a very small percentage of the total breast tissue.

Variable demagnification and automatic refocusing by the system 19 is very important in order to enable the physician to minimize the amount of exposure of the woman's breast to x-rays by the above procedure of first taking an x-ray of the entire breast, and after initial analysis, focusing the analysis on more magnified subsequent enlarged images of likely tumor or microcalcification sites, with minimum acceptable x-ray dosages. To understand how the x-ray dosage is reduced from an initial level in order to view a digitally marked region of breast 3, it would be helpful to refer to FIG. 4.

Figure 4:
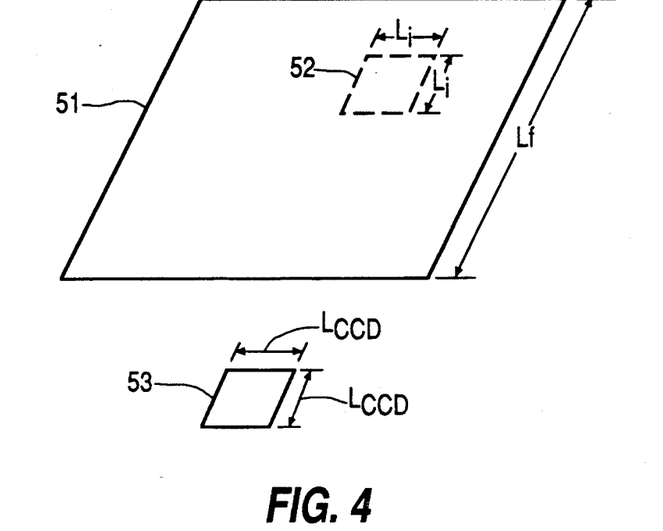
FIG. 4 is a diagram useful in explaining the operation of the apparatus of FIG. 2.

In FIG. 4, numeral 51 designates a field of view essentially fully occupied by breast 3. Field of view 51 is square, having a dimension of $L_f$ per side. $L_f$ may be 16 centimeters. Numeral 52 designates a digitally marked square region within field of view 51 having side dimensions of $L_i$, which may be 5 centimeters for a typically region of interest. Numeral 53 designates a square CCD detector array in cooled, slow scan CCD camera 20 having dimensions of $L_{CCD}$ per side.

Next, it should be understood that if the x-ray dosage is kept constant, and cooled, slow scan CCD camera 20 is moved so that the entire field of view 51 is focused onto CCD array 53, the mean intensity of detected light signals impinging thereon is given by equation $$I_f = k \left( \frac{m1}{m1 + 1} \right)^2. \tag{1}$$

$$\text{where } m1 = \frac{L_{CCD}}{L_f}.$$

Then, if the camera is moved so that only the area of interest 52 receives the x-ray dosage, then the mean intensity in the area of interest 52 is given by $$I_i = k \left( \frac{m2}{m2 + 1} \right)^2. \tag{2}$$

$$\text{where } m2 = \frac{L_{CCD}}{L_i}.$$

Then the ratio of $I_i$ to $I_f$ represents the amount that the x-ray dosage, and hence the exposure time, can be reduced and still provide a sufficient intensity of light in response to x-rays passing through the digitally marked region 52 to distinguish tumors, microcalcifications, etc. from adjacent healthy tissue. This ratio is given by $$\frac{I_i}{I_f} = \left( \frac{m2(m1 + 1)}{m1(m2 + 1)} \right)^2. \tag{3}$$

For the example of the values of $L_f$, $L_i$, and $L_{CCD}$ given above, equation (3) shows that the x-ray exposure time can be reduced by a factor of 6.6 for imaging a 5 centimeter by 5 centimeter digitally marked area.

Figure 5:
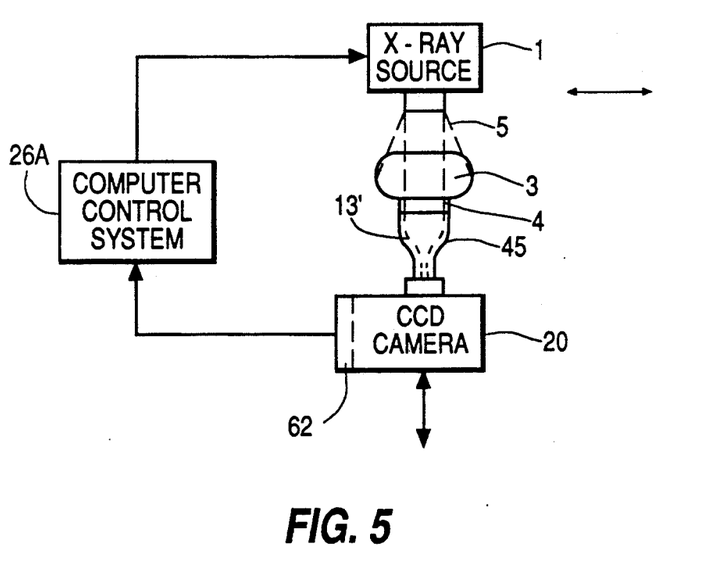
FIG. 5 is a diagram of a system similar to that of FIG. 2, with a fiber optic reducer replacing the lens coupling system of FIG. 2.

FIG. 5 shows an alternate embodiment similar to that of FIG. 2, in which the optical interface 18 is replaced by a fiber optic reducer 45. In this embodiment of the invention, greater sensitivity is achieved.

In FIG. 5, fiber optic reducer 45 may have substantially smaller top surface area than the area of tissue 3 to be evaluated. For example, the dimensions of the top surface of fiber optic reducer 45 may be approximately 2 inches by 3 inches. Phosphor screen 4 is coextensive with the top surface of fiber optic reducer 45. The lower end of fiber optic reducer 45 feeds light concentrated from phosphor screen 4 into cooled, slow scan CCD camera 20. The apparatus supporting cooled, slow scan CCD camera 20 and fiber optic reducer 45 is moved horizontally in two dimensions, and multiple exposures by x-ray source 1 are made and detected by cooled, slow scan CCD camera 20 to evaluate the entire tissue mass 3.

It can be easily shown that the light collection efficiency when using a fiber optic reducer as in FIG. 5 is approximately ten times greater than the collection efficiency using the lens-coupled arrangement shown in FIG. 2. Therefore, the embodiment of FIG. 5 is capable of achieving both lower x-ray doses to patients and higher resolution images than the embodiment of FIG. 2.

In the embodiment of FIG. 5, the continuous read out of the contents of serial register 62, which is exposed to essentially the same incoming light levels as the parallel array 61 (see FIG. 6), results in continuous measurement of the present x-ray dosage during exposure and collection of image information by the parallel array 61.

It should be noted that a combination of the above-described lens coupled interface and the above-described fiber optic reducer interface could be advantageously used in some applications. In an application where a large field of view is required, the image captured by the lens is optically coupled to the CCD array by means of a fiber optic reducer.

Figure 6:
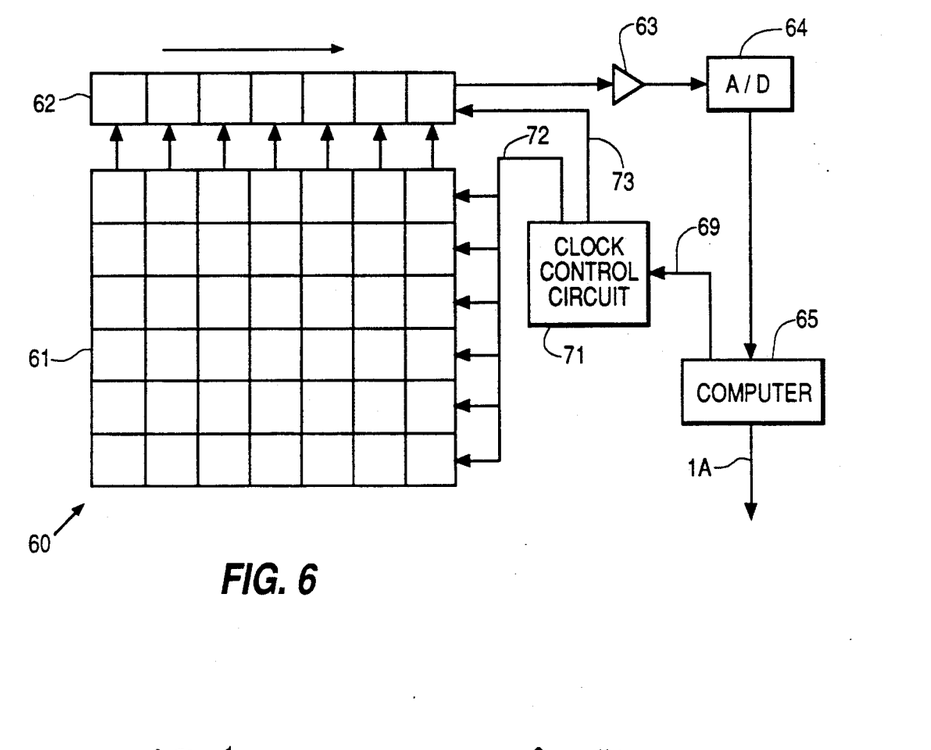
FIG. 6 is a diagram of a CCD dose measuring apparatus that can be used in the embodiment of the invention shown in FIGS. 2 and 5, and also in other dose measuring applications.

In FIG. 6, numeral 60 designates a CCD dose measuring apparatus including a rectangular or "parallel" array 61 of CCD cells. Serial register 62 includes a single row of CCD cells each of which is connected to a corresponding receptor from all of the CCD cells in a column of parallel CCD array 61. During readout of an image from parallel array 61 readout of the information imaged onto parallel array 61 is accomplished one row at a time by shifting successive rows, one at a time, into serial register 62 and serially shifting the contents of serial register 62 via a buffer amplifier 63 into the input of an analog-to-digital converter circuit 64. Computer 65 controls readout of serial register 62 by supplying control signals 69 to clock control circuit 71. In response to signals 69, clock control circuit 71 produces readout signal 73 which are applied to the cells of register 62. Clock control circuit 71 also produces clock signals 72 which are applied to the parallel registers 61. During exposure, no clock signals 72 are applied to the parallel registers 61, which are accumulating charge in response to the incident light received, and signals 73 are repetitively applied to the cells of serial register 62 to monitor accumulated light exposure. The digital output of analog-to-digital converter 64 is read by a computer 65, which assembles and stores image information. In the prior art, the collection of incoming light by serial register 62 is deemed to be problematic.

In some cases, the charging up of the cells of serial register 62 causes a leakage current into parallel array 61, producing data errors. Also, the first scan of data from serial register 62 frequently produces errors. In accordance with the present invention, the dosage measuring device 60 permits continuous measurement of the accumulated x-ray dosage without disturbing the image data being collected by the parallel array 61.

In accordance with one embodiment of the invention, while the CCD cells of parallel array 61 are being imaged, the CCD cells of serial register 62 also receives and are charged up by the incoming light. The charge thereby accumulated on the CCD cells of serial register 62 represents the accumulated x-ray dosage. Computer 65 receives corresponding digital dosage information, computes the present dosage, and generates an inhibit signal IA to terminate the dosage being produced by x-ray source 1 as soon as a certain minimum acceptable threshold dosage level has been achieved.

Figure 8:
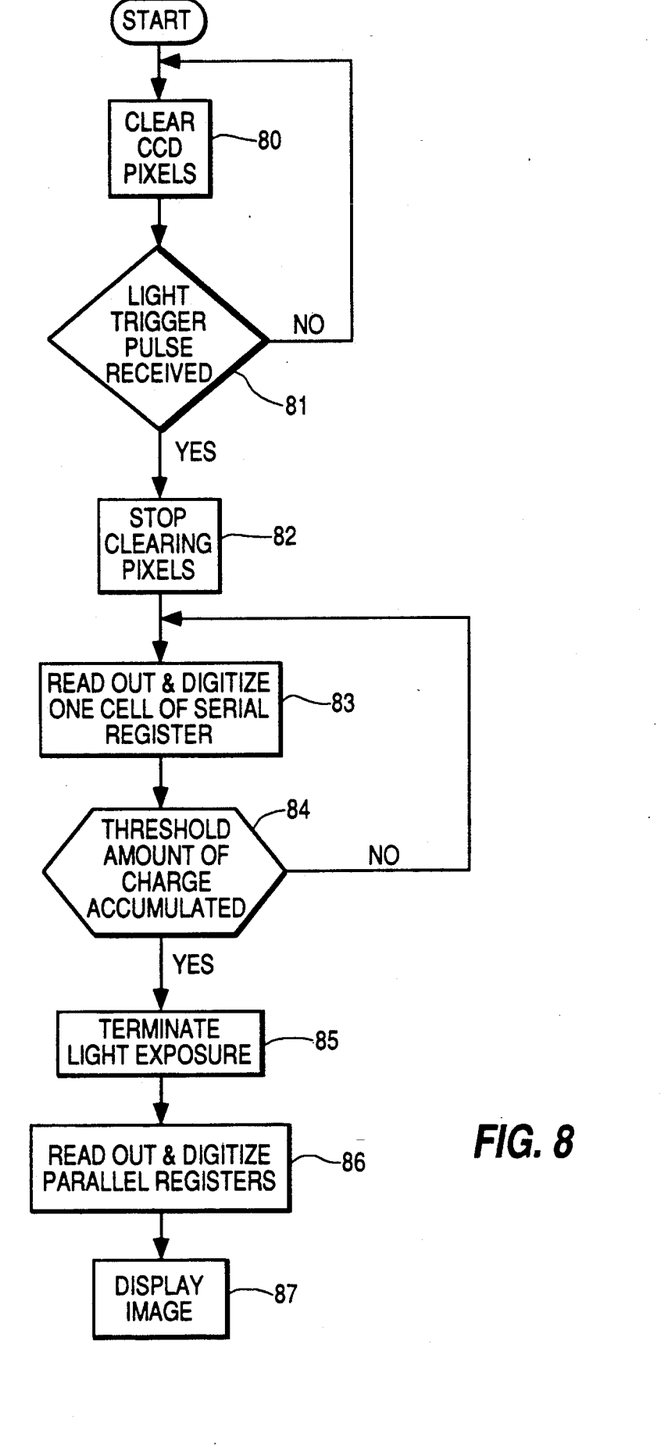
FIG. 8 is a flowchart useful in describing the operation of the embodiment of FIG. 6.

FIG. 8 is a flowchart of a simple routine that can be executed by computer 65 to effectuate monitoring the accumulated light exposure received by parallel array 61. The routine first enters block 80 and issues signals via bus 69 to clear all of the cells in parallel register 61 and serial register 62. The routine then goes to decision block 81 and waits for an external signal indicating that light exposure has begun. If the determination of decision block 81 is negative, the routine returns to the entry point of block 80. If the determination of decision block 81 is affirmative, the routine goes to block 82 and causes conventional clock control circuitry 71 to stop clearing the cells of parallel register 61 and serial register 62. The routine then goes to block 83 and issues commands to clock control circuitry 71 causing it to produce appropriate clocking signals 73 to serial register 62 in order to cause it to read out and digitize each of the individual cells of serial register 62.

Then the routine goes to decision block 83 and determines if a predetermined amount of charge has been accumulated in at least some of the cells referred to in block 84. If not, the routine returns to the entry point of block 83. If the predetermined amount of charge has been accumulated, the routine goes to block 85 and causes computer 65 to generate a signal that terminates the light exposure. The routine then goes to block 86, wherein computer 65 issues signal to cause clock control circuitry 71 to produce signals 73 and 72 in order to read out and digitize all of the cells of parallel register 61. If appropriate, the digitized results are displayed, as indicated in block 87.

Returning to FIG. 5, the "serial register" portion 62 of cooled, slow scan CCD camera 20 is read out and evaluated by computer control system 26A to determine when an adequate amount of light 13' has been received from phosphor screen 4 to produce an image of suitable resolution. Computer control system 26A then generates a signal IA to automatically terminate or reduce the dosage produced by x-ray source 1. This technique also can be used to reduce the dosage produced by x-ray source 1 in the embodiment of FIG. 2, rather than by executing the root mean square noise ratioing technique described above.

The above-described system is especially useful in conjunction with the previously described radiopaque needle localization, because the digital image, with high signal-to-noise ratio and high contrast resolution may be obtained almost instantly, rather than having to wait several minutes for a radiographic film development process to be performed. A trial-and-error process for locating the tip of the radiopaque needle precisely at the tumor locations (in order to enable accurate surgical removal of a biopsy specimen at the correct location) can be performed much more rapidly because the present location of the needle tip is very quickly, almost instantly, converted to digital data that is compared with the digitally marked possible tumor locations. The x-ray dosage during the needle localization procedure can be reduced to a very low level at which only the needle, but not the tissue, is imaged. After the radiopaque needle has been positioned at precisely the site of a digitally marked possible tumor location, the surgical removal of the biopsy sample can be performed. If needle aspiration techniques are used to remove tissue, the x-ray dosage can be reduced to a very low level at which only the aspiration needle is imaged.

The great reduction in the amount of time results in much less inconvenience and discomfort to the patient who must sit motionless during the entire procedure.

Thus, automatic focusing system 19 enables control system 26 to instruct x-ray source 1 how much to reduce the x-ray dosage in response to accurate measurements of signal-to-noise ratio for various focus settings, as described above. The x-ray dosage can be computed from the intensity received by serial register in the cooled, slow scan CCD camera.

An advantage of the embodiment of the invention shown in FIG. 5 is that contrast resolution exceeding that achievable with radiographic film is obtained. This advantage is achieved because of the accuracy achievable with available CCD cooled cameras and slow scanning techniques, in combination with use of the fiber optic reducer.

Figure 7:
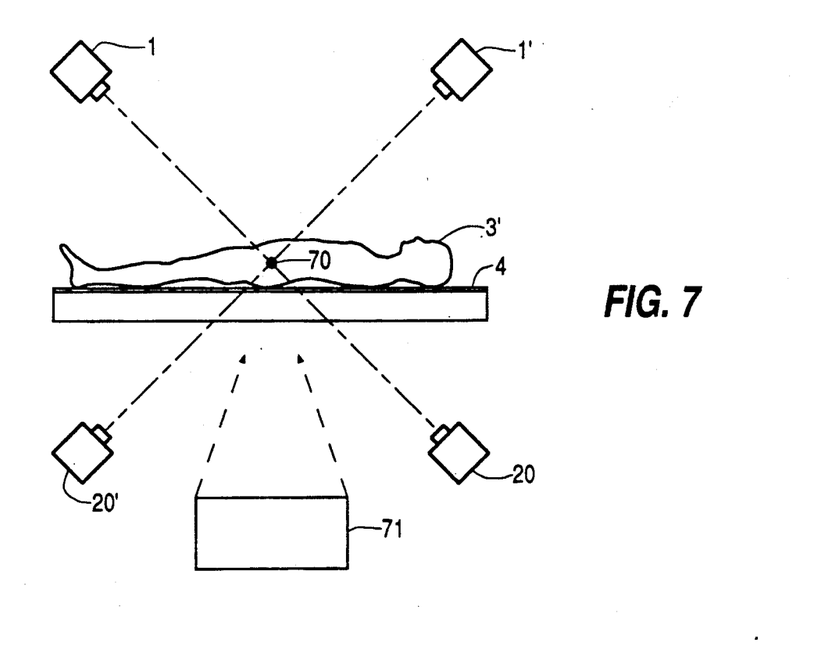
FIG. 7 is a diagram useful in describing application of the invention to lithotripsy.

Another application of the invention is illustrated in FIG. 7, wherein a patient 3' is supported on phosphor screen 4. An x-ray source 1 produces an x-ray beam 5 the center axis of which passes through kidney stone 70. Cooled, slow scan CCD camera 20 reads the data and inputs it to a computer (not shown) which rapidly generates an accurate image thereof. A dosage measuring technique similar to either of the ones described above is utilized to terminate the exposure by x-ray source 1 when an adequate level of light has been received by cameras 20 from phosphor screen 4. X-ray source 1 is tilted to the alternate position indicated by numeral 1' and aimed so that the center axis of x-ray source 1 passes through kidney stone 70 from a different angle. The resulting images are captured by cameras 20. The computer scanning cooled, slow scan CCD cameras 20 then can generate accurate three-dimensional data precisely locating kidney stone 70. The amount of time the patient is subjected to anesthesia is reduced, and his exposure to x-rays is reduced.

While the invention has been described with reference to several particular embodiments thereof, those skilled in the art will be able to make the various modifications to the described embodiments of the invention without departing from the true spirit and scope of the invention. For example, the technique of the invention can be applied to various other body parts.

What is claimed is:

1. A radiology device for imaging tissue, comprising:
   (a) a controlled x-ray source for directing x-rays through the tissue;
   (b) a screen positioned to receive x-rays existing from the tissue for producing a light image in response to the exiting x-rays;
   (c) a cooled, slow scan CCD camera;
   (d) means for optically coupling light emitted by the screen into said CCD camera;
   (e) means for operating said camera to produce analog information representing an image of the tissue and means for converting the analog information to digital information;
   (f) means for storing the digital information as a representation of the light image in response to the digital information;
   (g) means for marking a location of a portion of said light image having at least a certain density variation;
   (h) means for reducing the x-ray dosage to a level at which an image of predetermined resolution of the marked portion is produced;
   (i) wherein said reducing means reduces the x-ray dosage to a level at which only a radiopaque needle inserted into a digitally marked region is imaged;
   (j) said reducing means including means for reducing the x-ray dosage by the ratio $$\frac{I_i}{I_f} = \left( \frac{m2(m1 + 1)}{m1(m2 + 1)} \right)^2,$$

where $m1 = \dfrac{L_{CCD}}{L_f}$  where $m2 = \dfrac{L_{CCD}}{L_i}$ where $L_f$ is the width of the field of view of the cooled, slow scan CCD camera, $L_i$ is the width of a region of interest within the field of view, and $L_{CCD}$ is the width of a rectangular CCD detector array in the cooled, slow scan CCD camera.

2. A device for imaging tissue, comprising:
   x-ray a controlled source for directing x-rays through x-ray transmissive tissue of given dosages;
   an x-ray sensitive screen for forming an image in response to x-rays passing through the tissue;
   optical means optically coupled to said screen for forming digital signals representing a selected portion of the image;
   said optical means including field-of-view varying means for defining the size and location of the selected portion; and
   control means responsive to the digital signals for reducing the level of the x-ray dosage of said x-ray source by an amount corresponding to the reduction in size of the selected portion with respect to the size of the original field of view.

3. The device of claim 2 wherein the device includes a cooled, slow scan CCD camera and the x-ray dosage control means includes means for reducing the x-ray dosage by the ratio $$\frac{I_i}{I_f} = \left( \frac{m2(m1 + 1)}{m1(m2 + 1)} \right)^2,$$

where $m1 = \dfrac{L_{CCD}}{L_f}$  where $m2 = \dfrac{L_{CCD}}{L_i}$ where $L_f$ is the width of the field of view of the cooled, slow scan CCD camera, $L_i$ is the width of a region of interest within the field of view, and $L_{CCD}$ is the width of a rectangular CCD detector array in the cooled, slow scan CCD camera.

* * * * *